US008692878B2

United States Patent
Chen et al.

(10) Patent No.: US 8,692,878 B2
(45) Date of Patent: Apr. 8, 2014

(54) METHODS AND APPARATUS FOR SIMULTANEOUSLY INSPECTING MULTIPLE ARRAY REGIONS HAVING DIFFERENT PITCHES

(75) Inventors: Hong Chen, San Ramon, CA (US); Jason Z. Lin, Saratoga, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 488 days.

(21) Appl. No.: 13/062,934

(22) PCT Filed: Jun. 18, 2010

(86) PCT No.: PCT/US2010/039238
§ 371 (c)(1),
(2), (4) Date: Mar. 8, 2011

(87) PCT Pub. No.: WO2010/148343
PCT Pub. Date: Dec. 23, 2010

(65) Prior Publication Data
US 2011/0164130 A1    Jul. 7, 2011

Related U.S. Application Data

(60) Provisional application No. 61/218,913, filed on Jun. 19, 2009.

(51) Int. Cl.
*H04N 7/18* (2006.01)
(52) U.S. Cl.
USPC .......................................... 348/126; 250/310
(58) Field of Classification Search
USPC .......................................... 250/310; 348/126
See application file for complete search history.

(56) References Cited

U.S. PATENT DOCUMENTS 7,037,735 B2 * 5/2006 Noguchi et al. ................ 438/18
7,065,239 B2   6/2006 Maayah et al.
(Continued)

FOREIGN PATENT DOCUMENTS

JP    2006-216611    8/2006
JP    2006-226833    8/2006

OTHER PUBLICATIONS

PCT International Search Report for Application No. PCT/US2010/039238, 3 sheets, Jan. 4, 2011.
(Continued)

*Primary Examiner* — Sath V Perungavoor
*Assistant Examiner* — Jeffery Williams
(74) *Attorney, Agent, or Firm* — Okamoto & Benedicto LLP (57) ABSTRACT

One embodiment relates to a method of automatically inspecting multiple array regions (102) simultaneously using an imaging apparatus (302). The method includes selecting (211 or 212) an optimal pixel size such that each array region in the multiple array regions has a grouped cell which is an integer number of pixels in size, and adjusting a pixel size of the imaging apparatus to be the selected optimal pixel size. Optimal pixel sizes within an available range of pixel sizes may be determined by finding (202) a largest common divider of cell sizes of the multiple array regions when the cell sizes are expressed in integers. Pre-set criteria may be applied to determine (208) which, if any, of the optimal pixel sizes are acceptable based on pre-set criteria. If none of the optimal pixel sizes are acceptable, then one of the array regions may be marked for digital interpolation (see 216). Other embodiments, aspects, and features are also disclosed.

24 Claims, 3 Drawing Sheets

(56) References Cited

U.S. PATENT DOCUMENTS 7,379,580 B2 5/2008 Levin et al.
7,397,941 B1 7/2008 Adler
2005/0173634 A1 8/2005 Wong et al.
2006/0258024 A1* 11/2006 Brodsky et al. ............... 438/14

OTHER PUBLICATIONS

PCT International Preliminary Report on Patentability for Application No. PCT/US2010/039238, 5 sheets, Dec. 20, 2011.

* cited by examiner

METHODS AND APPARATUS FOR SIMULTANEOUSLY INSPECTING MULTIPLE ARRAY REGIONS HAVING DIFFERENT PITCHES

CROSS-REFERENCE TO RELATED APPLICATION

The present application claims priority to U.S. Provisional Patent Application No. 61/218,913, filed on Jun. 19, 2009, which is incorporated herein by reference in its entirety.

BACKGROUND

1. Technical Field

The present invention relates generally to wafer and reticle inspection apparatus and methods of using same.

2. Description of the Background Art

Automated inspection and review systems are important in process control and yield management for the semiconductor and related microelectronics industries. Such systems include optical and electron beam (e-beam) based systems.

In the manufacture of semiconductor devices, detection of defects early on in the development and fabrication process is becoming increasingly important to shorten product development cycles and increase manufacturing yield. Advanced wafer and reticle inspection systems are being used to detect, review and classify defects and feed the root cause information back into the manufacturing process to prevent these defects going forward. The size of relevant defects is directly proportional to the design rule being applied to the manufacturing of the semiconductor devices. As the design rule being applied continues to shrink, the performance demands on inspection systems increases both in terms of imaging resolution and speed (defects processed per hour).

SUMMARY

One embodiment relates to a method of automatically inspecting multiple array regions simultaneously using an imaging apparatus. The method includes selecting an optimal pixel size such that each array region in the multiple array regions has a grouped cell which is an integer number of pixels in size, and adjusting a pixel size of the imaging apparatus to be the selected optimal pixel size. Optimal pixel sizes within an available range of pixel sizes may be determined by finding a largest common divider of cell sizes of the multiple array regions when the cell sizes are expressed in integers. Pre-set criteria may be applied to determine which, if any, of the optimal pixel sizes are acceptable based on pre-set criteria. If none of the optimal pixel sizes are acceptable, then one of the array regions may be marked for digital interpolation.

Another embodiment relates to an inspection apparatus for detecting defects in a plurality of array regions on a manufactured substrate. The inspection apparatus includes an imaging apparatus and a system controller. The imaging apparatus is arranged to illuminate an area of the substrate and to detect image data from the area, wherein the area includes a set of multiple array regions. The system controller includes a processor, memory and computer-readable code in said memory. The computer-readable code is configured to select an optimal pixel size such that each array region in the multiple array regions has a grouped cell which is an integer number of pixels in size, and to adjust a pixel size of the imaging apparatus to be the selected optimal pixel size.

Other embodiments, aspects and features are also disclosed.

DETAILED DESCRIPTION

Electron beam (e-beam) and optical imaging apparatus are utilized for inspection of manufactured substrates, such as semiconductor wafers and reticles for lithography. Certain of these substrates are designed to include one or more array regions, where each array region comprises an array of cells which are designed to be identical.

Conventional imaging apparatus have been utilized to efficiently inspect a single array region of identically-designed cells. However, applicants have determined that conventional imaging apparatus have a substantial drawback or limitation when applied to image a semiconductor die with multiple array regions having different array cell sizes.

The present application discloses improved methods and apparatus for simultaneously inspecting multiple array regions having different array cell sizes.

Inspecting a Single Array Region

In inspection tools from KLA-Tencor Corporation of Milpitas, Calif., a current method for inspecting a single array region which consists of identically-designed cells of a single size involves adjusting a nominal pixel size with optical zoom so that the number of pixels in a single cell (in each dimension) is an integer. With an integer number of pixels in a single cell, cell-to-cell comparison can be performed to achieve optimal sensitivity in defect detection using various defect detection algorithms, such as automatic thresholding (AT), segmented automatic thresholding (SAT) or multiple die automatic thresholding (MDAT).

Inspecting Multiple Array Regions Having Different Cell Sizes Simultaneously

As the circuits in the wafer get denser and more highly integrated, multiple array regions having different cell sizes (i.e. different pitches) appear more and more commonly in the dies of an advanced wafer or reticle. As a result, the current method requires setting up multiple separate imaging scans, one for each array region. Each imaging scan needs to be tailored for a single array region with a specific cell size in order to achieve optimal sensitivity in each array region. The throughput of inspection is thus compromised because of the need for multiple imaging scans to inspect the multiple array regions.

One method for overcoming the throughput issue is to inspect the multiple array regions having different pitches using a random inspection technique for die-to-die comparison, instead of cell-to-cell comparison. The disadvantage is that the defect detection sensitivity becomes degraded because of more process variation from die to die and the extra noise contributed by digital interpolation in performing die-to-die alignment.

Another method for inspecting the multiple array regions having different pitches, without sacrificing throughput, is as follows. First, a pixel size is selected which makes the pitch (in each dimension) of a single array region correspond to an integer number of pixels. Cell-to-cell alignment is then performed for the remaining array regions by digital interpolation of the image data so that the cell-to-cell comparison may be performed for the remaining array regions under the selected pixel size. This approach, however, suffers from a similar drawback as the die-to-die comparison method. This is because the defect detection sensitivity in the remaining array regions is compromised due to the extra noise contributed by the digital interpolation.

The present application discloses an innovative technique for inspecting multiple array regions that have different cell sizes on a single die. A method is disclosed which enables the determination and selection of a particularly advantageous pixel size for inspecting the multiple array regions simultaneously. The selected pixel size minimizes the number of array regions requiring digital interpolation for cell-to-cell alignment. As such, the extra noise due to digital interpolation may be avoided, and a high throughput rate for the inspection system may be sustained.

The following description discloses an innovative technique for selecting an optimal pixel size. For ease of discussion, this technique is discussed in terms of one dimension of the array regions. As one of ordinary skill in the art will recognize, array regions are two dimensional. Hence, the technique should be applied to select an optimal pixel size in each of the two dimensions.

Forming Grouped Cells by Grouping Multiple Cells in Each Array Region

Figure 1:
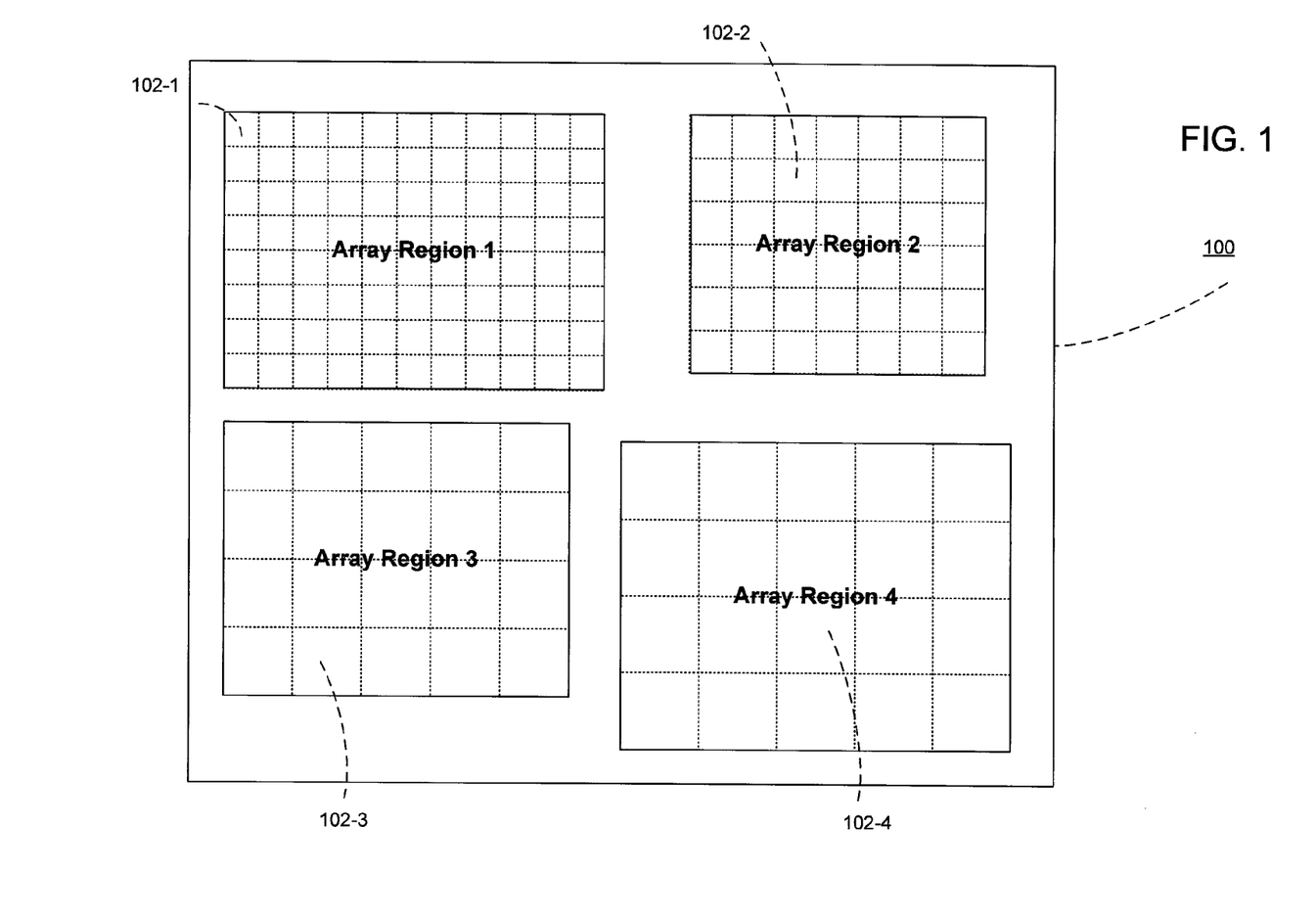
FIG. 1 is a diagram depicting an example of multiple array regions within a single field of view.

FIG. 1 shows an example of a field of view 100 with four array regions to be inspected at the same time. The four array regions in this example are labeled Array Region 1, Array Region 2, Array Region 3 and Array Region 4. These array regions may be located, for example, on a single semiconductor die. Each array region is made up of cells (102-1, 102-2, 102-3, and 102-4 for Array Regions 1, 2, 3 and 4, respectively) which are designed to be identical to the other cells in the same array region. In general, the cells may be rectangular shaped. (For purposes of ease of illustration, each array region is shown as being several cells long in each dimension. However, actual array regions typically comprise a substantially higher number of cells along each dimension.) It is desirable to be able to inspect all four of the array regions at a same time, without the need to make multiple image scans.

In the following discussion, both the cell sizes and the pixel sizes are expressed in the smallest unit in which they can be expressed as integer numbers. For example, the smallest unit may be a nanometer (nm).

As given in Table 1, the four array regions may have cell sizes of 1044 nanometers (nm), 1278 nm, 2052 nm and 2592 nm respectively. Consider an example inspection tool with a nominal pixel size of 160 nm. Using the nominal pixel size for inspection, the cell size in pixels for each region becomes 6.525, 7.9875, 12.825 and 16.2 pixels, respectively.

TABLE 1

| Array Region | Array Cell Size in nm | Array Cell Size in Pixels with Pixel Size 160 nm |
| --- | --- | --- |
| 1 | 1044 | 6.525 |
| 2 | 1278 | 7.9875 |
| 3 | 2052 | 12.825 |
| 4 | 2592 | 16.2 |

A straightforward method that can accomplish better detect detection sensitivity, without sacrificing throughput, for inspecting multiple array regions with different cell sizes is by grouping a number of cells in each array region together to form a grouped cell so that the number of pixels (along that dimension) of the grouped cell becomes an integer. In the example shown in Table 1, to make a cell size of 6.525 pixels into an integer number of pixels, 40 cells may be grouped together to form a grouped cell with a cell size of 261 pixels. Similarly, the remaining three array regions require 80 cells, 40 cells and 10 cells, respectively. Table 2 shows the number of cells grouped together, and the grouped cell size in pixels.

TABLE 2

| Array Region | Array Cell Size in nm | Number of Cells Grouped Together | Grouped Cell Size in Pixels with Pixel Size 160 nm |
| --- | --- | --- | --- |
| 1 | 1044 | 40 | 261 |
| 2 | 1278 | 80 | 639 |
| 3 | 2052 | 40 | 513 |
| 4 | 2592 | 10 | 162 |

As such, cells may be combined or grouped in each array region so that each grouped cell formed in a respective array region has an integer number of pixels.

In principle, the above-disclosed grouping method may achieve better sensitivity than the prior methods of die-to-die alignment or cell-to-cell alignment because no digital interpolation is required. This grouping method may be practically applied when the sizes of the grouped cells remain relatively small compared to the sizes of the array regions.

However, when the sizes of the grouped cells are relatively large compared to the sizes of the array regions, then an array region may contain only a few of the grouped cells. Having only a few grouped cells per array region limits the ability to make meaningful cell-to-cell comparisons. In fact, the inspection algorithm may require a minimum number of grouped cells in order for it to properly detect defects. Furthermore, the image pixel data is normally processed frame-by-frame during inspection. Hence, each frame also should contain at least three or even more grouped cells so that meaningful cell-to-cell comparisons may be made.

Changing or Adjusting the Pixel Size

To overcome the above-discussed limitations relating to the formation of grouped cells, the present application further discloses a technique for selecting an optimal pixel size which reduces the sizes of the grouped cells. As described below, by changing or adjusting the size of the pixel used for image capture, the number of cells that need to be grouped together may be substantially reduced. For example, the inspection apparatus may be configured so that the pixel size for the image frame captures may be adjusted by several percent (for instance, +/−6%) by means of an "optical zoom" (i.e. by changing a magnification of the imaging apparatus in each dimension). The adjustment range may vary depending upon the specific apparatus being used.

In accordance with an embodiment of the invention, the size of the pixel is changed or adjusted in such a way that, for each array region in the frame, the number of cells that need to be grouped together is substantially reduced. The adjustment of the pixel size takes into account the various relevant array regions so that no array region requires a grouped cell which is unacceptably large.

Consider the example discussed above in relation to Tables 1 and 2. Surprisingly, if the pixel size is adjusted with +1.25% from 160 nm to 162 nm by changing the magnification, the sizes of the grouped cells (in that dimension) may be greatly reduced.

Table 3 shows the integer number of pixels (in that dimension) for the grouped cell in each array region based on the adjusted pixel size of 162 nm. As seen, the number of cells grouped together in the four array regions (so that each grouped cell formed in a respective array region has an integer number of pixels in that dimension) is reduced to 9 cells, 9 cells, 3 cells and 1 cell, respectively. Correspondingly, the grouped cell size in pixels is substantially reduced.

TABLE 3

| Array Region | Array Cell Size in nm | Number of Cells Grouped Together | Grouped Cell Size in Pixels with Pixel Size 162 nm |
|---|---|---|---|
| 1 | 1044 | 9 | 58 |
| 2 | 1278 | 9 | 71 |
| 3 | 2052 | 3 | 38 |
| 4 | 2592 | 1 | 16 |

Selecting an Optimal Pixel Size for Inspecting Multiple Array Regions Simultaneously As described above, applicants have discovered that a small change adjustment in the pixel size can dramatically reduce the number of cells required to form a grouped cell of integer number of pixels. The present application further discloses techniques for selecting an optimal pixel size for inspecting multiple array regions at a same time.

One approach involves searching all possible pixel sizes within the adjustable range and then selecting an optimal pixel size that meets certain preset criteria. While this "brute force" approach will work, it can be quite inefficient. The present application describes a highly innovative approach which is described below. Applicants believe that this approach is quite efficient in typical scenarios.

Assuming that there are N array regions to be inspected at the same time and each array region has a cell size $C_i$ in nm, where i is a number ranging from 1 to N. The nominal pixel size for inspecting the array regions is P nm. The actual pixel size that is used to capture the image data may be adjusted within the range. For example, the range may be the nominal pixel size plus or minus a small percentage α.

As seen above in the example of Table 2, to make each array region have an integer number of pixels based on the nominal pixel size, a very large number of cells may have to be grouped together for each array region. Because it is desirable to have as small cell sizes as possible for cell-to-cell comparison, an optimal pixel size $P_o$ may be chosen to minimize the number of cells required to make each cell size $C_i$ contain an integer number of pixels for all array regions to be inspected simultaneously. In addition, the optimal pixel size $P_o$ must be within the adjustable range of the nominal pixel size P, i.e., $$P_{min} <= P_o <= P_{max}, \quad (1)$$

or $$(1-\alpha)P <= P_o <= (1+\alpha)P, \text{ if } P_{min}=(1-\alpha)P, \text{ and } P_{max}=(1+\alpha)P. \quad (Eq\ 2)$$

In addition to the limitation based on the adjustable range, there may be a limitation on how many cells can be grouped together in an array region due to the finite physical size of the region. Each array region may have a different physical size, so this limitation on the number of cells that may be grouped together may be different for each array region. Therefore, determining the optimal pixel size for all possible use cases becomes a complicated problem dependent on not only the cell sizes, but also on the array region sizes and potentially other system factors.

Figure 2:
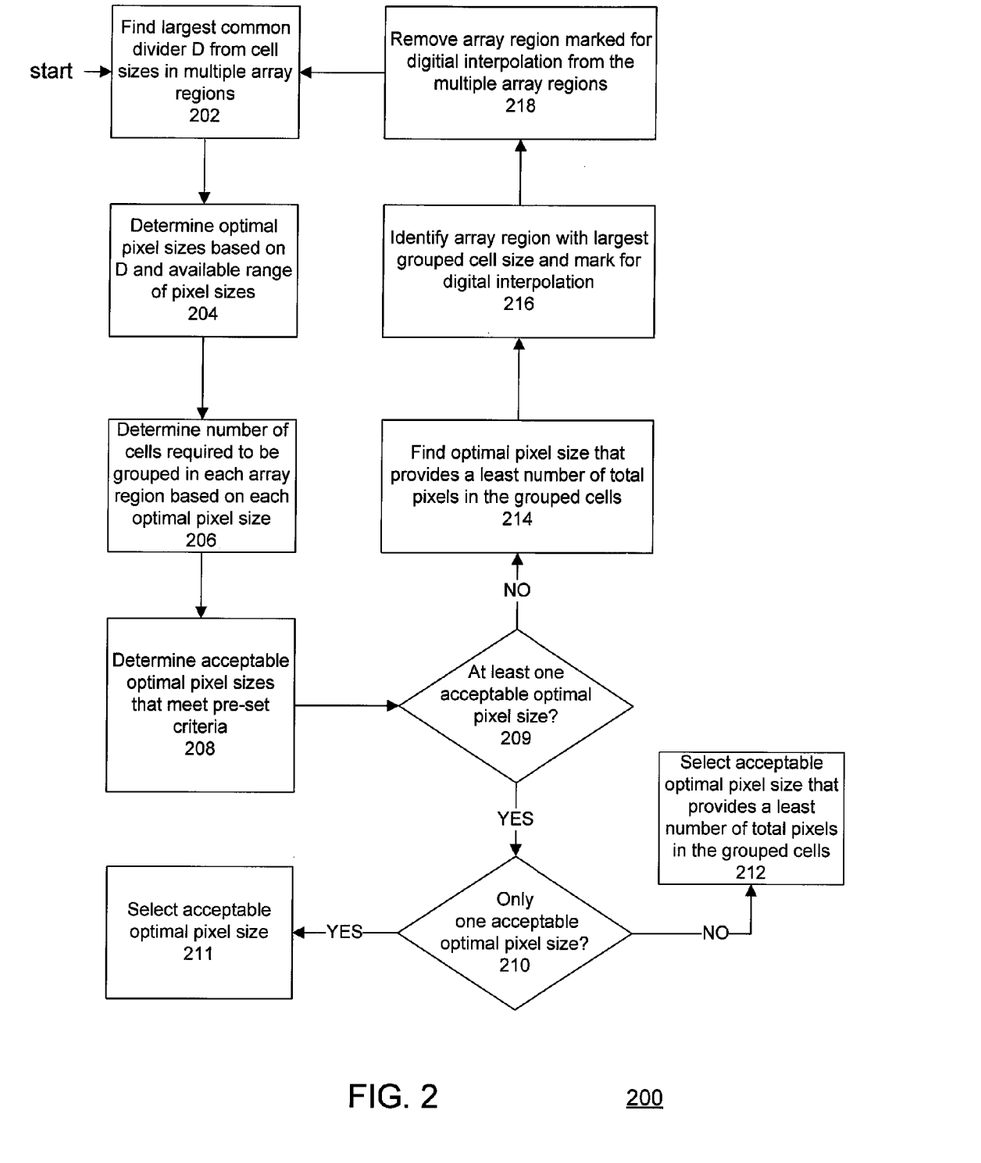
FIG. 2 is a flow chart depicting a method of selecting a pixel size for inspecting multiple array regions at a same time in accordance with an embodiment of the invention.

Given the above assumptions and considerations, FIG. 2 discloses a method 200 of selecting an optimal pixel size for inspecting multiple array regions at a same time in accordance with an embodiment of the invention. In a first step 202, the method 200 finds the largest common divider D in $C_i$ among all the array regions i, where i=1 to N. In other words, the largest common divider D is a largest integer that satisfies $C_i=K_iD$ for I=1 to N, where $K_i$ are integers.

In accordance with a next step 204, applicants have determined that if an integer divider of the largest common divider D can be found to satisfy the above equation which constrains the adjustable pixel size, then the integer divider will be an optimal (i.e. a candidate) pixel size $P_o$ with which each array region can have an integer number of pixels without having to group a number of cells together. In other words, if there exists a $P_o$ such that $D/P_o$ is an integer, and $$(1-\alpha)P <= P_o <= (1+\alpha)P, \quad (Eq\ 2)$$

then that $P_o$ is an optimal pixel size.

More generally, however, the largest common divider D may be a small number which has to be multiplied by some integer factor m before an integer divider can be found to satisfy the constraint of the adjustable pixel range. In other words, if there exists a $P_o$ such that $mD/P_o$ is an integer and $$(1-\alpha)P <= P_o <= (1+\alpha)P, \quad (Eq\ 2)$$

then $P_o$ is an optimal pixel size. This means that multiple cells in some or all array regions have to be grouped together so as to obtain an optimal pixel size that can provide an integer number of pixels for cell-to-cell comparison when all the array regions are inspected at the same time. In other words, the problem of determining the optimal pixel size becomes finding the integer factors m and n such that $$mD = nP_o \quad (Eq\ 3)$$

or $$P_o = (mD)/n \quad (Eq\ 4)$$

for $P_0$ within the adjustable pixel range, where both m and n are integers. Note that there may be multiple "optimal" pixel sizes $P_o$ that satisfy the above equation. In addition to determining the optimal pixel sizes $P_o$, the method 200 of FIG. 2 also selects one particular optimal pixel size for actual use in the simultaneous inspection of the multiple array regions. In this patent application, the particular optimal pixel size which is selected for actual use may be referred to as the "ideal" pixel size.

Per the next step 206, a determination is made as to the number of cells m required to be grouped in each array region based on each optimal pixel size $P_o$. Combining Equations 2 and 4 above, results in the following equations that must be satisfied:

$$(1-\alpha)P <= ((mD)/n) <= (1+\alpha)P; \quad (Eq\ 5)$$

or $$m <= n((1+\alpha)P/D) \quad (Eq\ 6a)$$

and $$m >= n((1-\alpha)P/D). \quad (Eq\ 6b)$$

In general, a smaller m provides better solution because it represents the number of cells needs to be grouped together to make the grouped cell an integer number of pixels. However, other limitations such as the frame size and the size of each array region as discussed above should also be considered before determining the ideal pixel size. Hence, a next step 208 involves determining acceptable optimal pixel sizes that meet pre-set criteria.

Take the use case shown in Table 1 as an example. The four array regions have cell sizes 1044 nm, 1278 nm, 2052 nm and 2592 nm respectively, and the nominal pixel size is 160 nm. The largest common divider among the four cell sizes can be found to be D=18. Assuming that the adjustable range of the nominal pixel size is 6%, i.e., $\alpha$=0.06. With the nominal pixel size P=160, the equations for determining the pixel size become:

$$m <= n((1+\alpha)P/D) = 9.42n \quad \text{(Eq 7a)}$$

and $$m >= n((1-\alpha)P/D) = 8.53n. \quad \text{(Eq 7b)}$$

Multiple solutions may be obtained from the above Equations 7a and 7b, such as, for example: (m=9, n=1), (m=26, n=3) and (m=28, n=3). Only a few of the solutions may have to be considered based on pre-set criteria, such as the frame size which limits the allowable maximum size of the grouped cell. In this example, assume that the above three solutions correspond to acceptable optimal pixel sizes $P_o$ which may be considered as candidates for the ideal pixel size. Using Equation 4, the acceptable optimal pixel sizes $P_o$ become 9*18/1=162 nm, 26*18/3=156 nm and 28*18/3=168 nm, respectively.

The above-described process may or may not determine at least one acceptable optimal pixel size. Per decision block 209, if there is at least one acceptable optimal pixel size, then a further decision block 210 determines whether there is only one acceptable optimal pixel size or whether there are more than one.

In some cases, there may be only one optimal pixel size that is deemed acceptable in that it alone satisfies all the pre-set criteria. In such a case, where there is only one acceptable optimal pixel size, that optimal pixel size is selected per step 211 for use in the simultaneous inspection of the multiple array regions.

In other cases, it may be possible that there are still multiple optimal pixel sizes that are acceptable. In such a case, the multiple optimal pixel sizes are all within the adjustable range of the nominal pixel size, and they also satisfy all the pre-set criteria so as to be acceptable so far. Under this circumstance, a final criterion may be applied to select the optimal pixel size for use in the image capture. Because in general the smaller the cell size, the better the defect detection sensitivity, one possible final criterion is that the optimal pixel size to be selected is the one that provides the least number of total pixels in the grouped cells from all the array regions. This criterion is somewhat arbitrary and can be changed if another criterion is more desirable.

Hence, if there is more than one acceptable optimal pixel size per decision block 211, then a final criterion may be applied to select which of those pixel sizes is to be selected. Per step 212, the pixel size selected may be the acceptable optimal pixel size that provides a least number of total pixels when the number of pixels in the grouped cells from all the array regions are summed together. Having a low number of total pixels in the grouped cells is preferable because it is desirable to have smaller cell sizes when making the cell-to-cell comparisons.

Continuing the above-discussed use case, the selected pixel size to be used turns out to be $P_0$=162 nm. This is because that pixel size corresponds to the least number of total pixels in the grouped cells.

It is worth mentioning that, although it appears that m is the number of cells that has to be grouped together to form a grouped cell of an integer number of pixels under the determined optimal pixel size, the number of cells required to be grouped together may actually be smaller in some array regions. As described earlier, the cell size in each array region can be expressed as $C_i = K_i D$. If $K_i$ and m have some common dividers, then the required number of cells can be reduced. Hence, the number of cells that needs to be grouped together in each array region can be determined by:

$$m_i = m/\epsilon(K_i, m) \quad \text{(Eq 8)}$$

where $\epsilon(K_i, m)$ represents the largest common divider between $K_i$ and m.

Returning to the decision block 209 of FIG. 2, there may be use cases where no optimal pixel size is found to be acceptable based on the pre-set criteria. Such a case may be due to one or more of the pre-set criteria not being met by any of the optimal pixel sizes. For example, the number of cells that have to grouped together in one or more array region may be too large to satisfy one or more pre-set criteria imposed by the maximum frame size, the minimum number of cells required by the inspection algorithm, or the limited physical size of the array region.

In this case, the method 200 may branch off and perform the step 214 in which an optimal pixel size is found that minimizes a total pixels in the grouped cells. In other words, this step 214 finds the optimal pixel size that has provided the least number of total pixels when the numbers of pixels in the grouped cells from all array regions are summed together. This particular optimal pixel size may then be utilized, per step 216, to identify an array region with a largest grouped cell size and mark that array region for digital interpolation. In other embodiments, another technique (other than given in steps 214 and 216) may be utilized to identify an array region for digital interpolation.

Per step 218, the array region that was marked for digital interpolation is removed from the set of multiple array regions being analyzed. Thereafter, the method 200 may loop back to step 202 and re-optimize the pixel size based on the remaining array regions so as to find an optimal pixel size that satisfies all the pre-set criteria based on the remaining array regions. The process may be repeated to further choose another array region for digital interpolation if that is necessary before an acceptable optimal pixel size can be found.

Pre-Set Criteria in Further Detail

As discussed above, pre-set criteria may be used for determining which optimal pixel sizes, if any, are acceptable for inspecting multiple array regions simultaneously. The pre-set criteria may be particularly useful in the case where the equations discussed above result in multiple optimal pixel sizes that are comparable. Let us now consider in further detail such pre-set criteria.

In accordance with an embodiment of the invention, the pre-set criteria may be based on certain limitations in implementing cell-to-cell comparisons for array inspection. In the practical implementation of cell-to-cell inspection, image pixels are usually divided into frames with each frame limited to a certain size to simplify algorithm implementation and memory management. In the inspection algorithm, there is usually also a requirement that a certain number of cells must exist in the frame so that the algorithm can be performed. Therefore, the frame size and the minimum number of required cells represent two important criteria that can be used to help determine the optimal pixel size for inspecting multiple array regions at the same time. Assuming that the frame size is limited to F pixels per frame, and the required minimum number of cells in the inspection algorithm is M cells, then number of pixels in the grouped cell size in each array region must be no greater than F/M.

In addition, each array region also has a limited physical size. As a result, the maximum number of cells available in the array region is another criterion that has to be satisfied. In order to be acceptable, an optimal pixel size must ensure that each array region has a sufficient number of grouped cells for inspection. In other words, if the inspection algorithm requires a minimum of M grouped cells, then each array region must be greater than the size of M grouped cells.

In summary, in addition to meeting the equations that described in the previous section, the optimal pixel size should also satisfy the following pre-set criteria. The optimal pixel size must result in the number of pixels in the size of the grouped cell in each array region no greater than F/M as defined above. In addition, the optimal pixel size is acceptable only if each array region is greater than the size of M grouped cells under the optimal pixel size. As a final criterion that may be used, the optimal pixel size should provide the least number of total pixels if the numbers of pixels in the grouped cells from all the array regions are summed together.

To illustrate a method using such pre-set criteria, consider an example having four array regions with the same cell sizes as shown in Table 1, but with the nominal pixel size being changed to 65 nm. Following the same equations described in the previous section, with nominal pixel size P=65, the equations for determining the pixel size become:

$$m \leq n((1+\alpha)P/D) = 3.83n \quad \text{(Eq 9a)}$$

and $$m \geq n((1-\alpha)P/D) = 3.39n. \quad \text{(Eq 9b)}$$

A few solutions can be obtained from the above equations, for example: (m=7, n=2), (m=11, n=3), (m=15, n=4), (m=17, n=5), (m=18, n=5), and (m=19, n=5). The corresponding pixel sizes (to the tenth of a nm) for these solutions are 63 nm, 66 nm, 67.5 nm, 61.2 nm, 64.8 nm and 68.4 nm, respectively. They are all within the 6% adjustable pixel range of 65 nm.

Table 4 shows the number of cells grouped together in each array region (in parenthesis) and the corresponding number of pixels in the grouped cell.

TABLE 4

| Array Cell Size in nm | pixel size | | | | | |
|---|---|---|---|---|---|---|
| | = 61.2 nm | = 63.0 nm | = 64.8 nm | = 66.0 nm | = 67.5 nm | = 68.4 nm |
| 1044 | 290 (17) | 116 (7) | 145 (9) | 174 (11) | 232 (15) | 290 (19) |
| 1278 | 355 (17) | 142 (7) | 355 (18) | 213 (11) | 284 (15) | 355 (19) |
| 2052 | 570 (17) | 228 (7) | 95 (3) | 342 (11) | 152 (5) | 570 (19) |
| 2592 | 720 (17) | 288 (7) | 40 (1) | 432 (11) | 192 (5) | 720 (19) |

Hence, as seen above, for the pixel size of 61.2 nm, for the array regions with cell sizes 1044 nm, 1278 nm, 2052 nm and 2592 nm, the number of cells grouped together is 17 in each array region, and the corresponding number of pixels in the grouped cells are 290, 355, 570 and 720, respectively. For the pixel size of 63.0 nm, for the array regions with cell sizes 1044 nm, 1278 nm, 2052 nm and 2592 nm, the number of cells grouped together is 7 in each array region, and the corresponding number of pixels in the grouped cells are 116, 142, 228 and 288, respectively. For the pixel size of 64.8 nm, for the array regions with cell sizes 1044 nm, 1278 nm, 2052 nm and 2592 nm, the number of cells grouped together are 9, 18, 3 and 1, respectively, and the corresponding number of pixels in the grouped cells are 145, 355, 95 and 40, respectively. And so forth.

To further determine which pixel size is an acceptable pixel size, assume that the frame size limit is 5000 pixels and that the required minimum number of cells (in this dimension) for the inspection algorithm is 5. This limits the maximum allowable grouped cell size as 5000/5=1000 pixels. All the pixel sizes shown in Table 4 appear to have satisfied this requirement.

Here, let us assume that these four array regions all have an identical physical size equal to approximately 150 microns, and therefore, the number of (ungrouped) cells in each array region is 143, 117, 73 and 57 respectively. As can be seen, pixel size 61.2 nm has to be ruled out because the inspection algorithm requires a minimum of 5 grouped cells, i.e., 17×5=85 (ungrouped) cells, but the third and fourth array regions only have 73 cells and 57 cells, respectively. Similarly, pixel size 68.4 nm has to be ruled out.

Choosing from among the remaining four candidate pixel sizes may be accomplished by applying the criterion that the optimal pixel size should provide the least number of total pixels if the numbers of pixels in the grouped cells from all the array regions are summed together. Based on this final criterion, the optimal pixel size 64.8 nm is selected.

Now consider a different situation in which the required minimum number of cells (in this dimension) for the inspection algorithm is 7. In this use case, the solution would be different. First of all, the maximum allowable grouped cell size becomes 5000/7=714 pixels which rule out pixel sizes 61.2 nm and 68.4 nm. Pixel sizes 64.8 nm and 66 nm are also ruled out because some array regions do not have enough number of ungrouped cells. Finally, based on the final criterion that the optimal pixel size should provide the least number of total pixels if the numbers of pixels in the grouped cells from all the array regions are summed together, the optimal pixel size 63.0 nm is selected.

Consider yet another scenario where the required minimum number of cells (in this dimension) for the inspection algorithm is 11. In this case, there would be no optimal pixel size that can be used for inspecting all array regions at the same time. This is because, regardless of which pixel size is used, there are some array regions that do not have a sufficient number of ungrouped cells. For example, pixel size 64.8 nm appears to be the closest solution which provides the least number of total pixels if the numbers of pixels in the grouped cells from all the array regions are summed together. However, the second array region does not have enough cells.

SUMMARY OF THE METHOD

In accordance with an embodiment of the invention, the method of selecting an optimal pixel size for use in inspecting multiple array regions at the same time may be summarized as follows.

1. Find the largest common divider from the cell sizes of the multiple array regions. (See step 202 in FIG. 2.)

2. Determine the candidate pixel sizes based on the largest common divider and the adjustable range of the nominal pixel size of the inspection. (See step 204 in FIG. 2.)

3. Determine the number of cells required to be grouped together in each array region based on each candidate pixel size. (See step 206 in FIG. 2.)

4. Determine all acceptable pixel sizes from the candidate pixel sizes which meet all pre-set criteria based on the maximum frame size, minimum number of cells required in the inspection algorithm, and the number of cells required to be grouped together, as well as the number of cells available in each array region. (See step 208 in FIG. 2.)

5. From all acceptable pixel sizes, find the pixel size that provides the least number of total pixels when the numbers of pixels in the grouped cells from all the array regions are summed together and continue step 8 if there are acceptable pixel sizes in step 4. (See steps 208 and 212 in FIG. 2.)

6. From all candidate pixel sizes, find the pixel size that provides the least number of total pixels if the numbers of pixels in the grouped cells from all the array regions are summed together if there are no acceptable pixel sizes in step 4. (See step 214 in FIG. 2.)

7. Identify the array region which has the largest grouped cell size among the multiple array regions, mark the array region as an array region for digital interpolation, and repeat steps 1 to 7. (See steps 216 and 218 in FIG. 2.)

8. If the pixel size can be found in step 5, an acceptable optimal pixel size has been found for inspecting the multiple array regions at the same time, with no or some array regions using digital interpolation. (See steps 208 and 212 in FIG. 2.)

Example Apparatus

Figure 3:
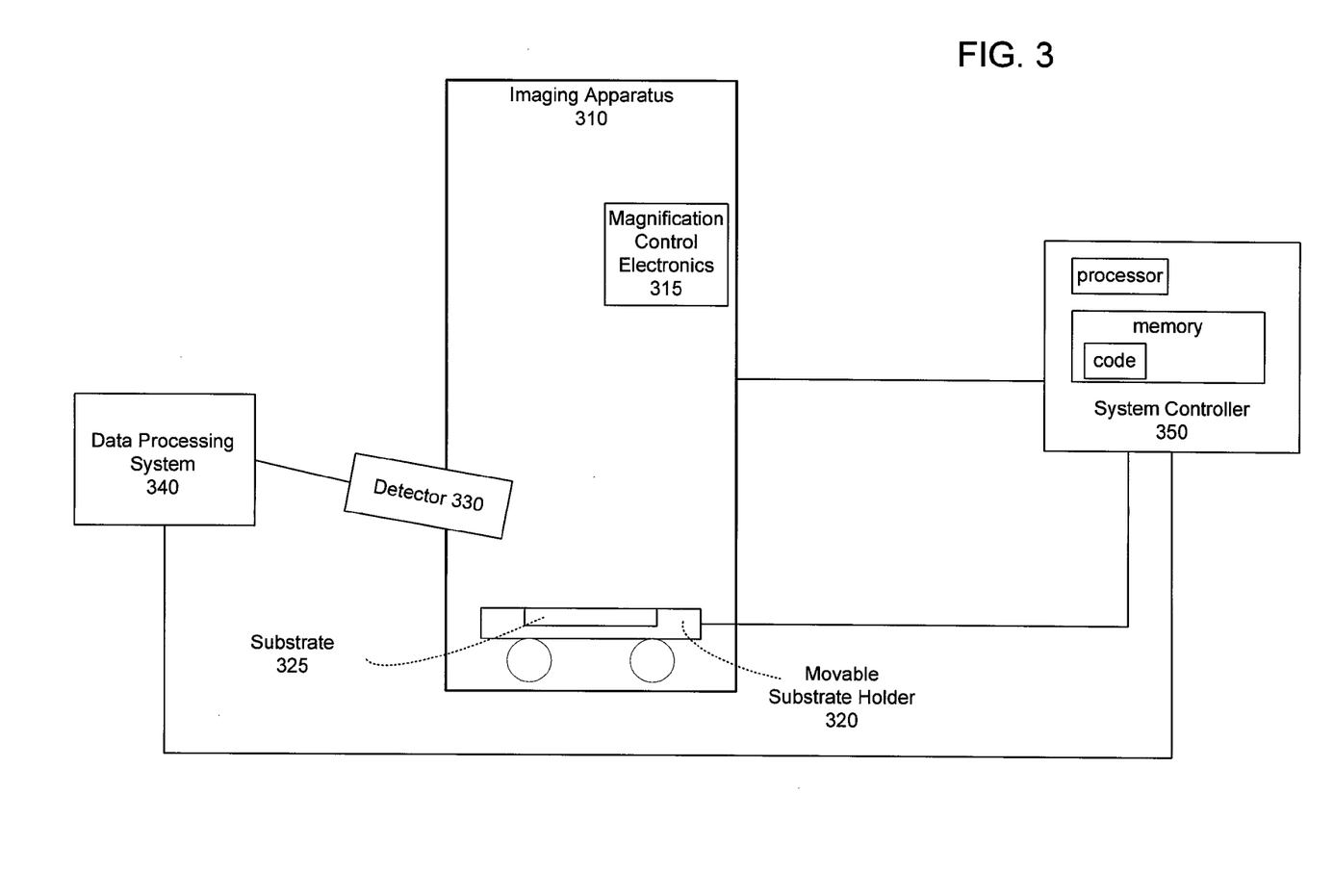
FIG. 3 is a schematic diagram of an inspection apparatus that may be utilized for automatically inspecting manufactured substrates in accordance with an embodiment of the invention.

FIG. 3 is a schematic diagram of an inspection apparatus that may be utilized for inspection of manufactured substrates in accordance with an embodiment of the invention. As shown in FIG. 3, the inspection apparatus includes an imaging apparatus 310, a movable substrate holder 320, a detector 330, a data processing system 340, and a system controller 350.

In one embodiment, the imaging apparatus 310 comprises an electron beam imaging apparatus. In an alternate embodiment, the imaging apparatus 310 comprises an optical imaging apparatus. In accordance with an embodiment of the invention, the imaging apparatus 310 includes electronics 315 to control and adjust the magnification of the imaging.

The movable substrate holder 320 may comprise a translatable mechanism to hold a target substrate 325. The target substrate 325 may be, for example, a semiconductor wafer or a reticle for lithography. The detector 330 is an appropriate detector for the particular imaging apparatus, and the data processing system 340 is configured to process image data from the detector 330.

The system controller 350 may include a processor, memory for storing processor-executable code and data, and various other components, such as a system bus, data storage system, input/output interfaces, and so forth. The system controller 350 may be communicatively coupled to the imaging apparatus 310 so as to electronically control the operation of the imaging apparatus 310. In accordance with an embodiment of the invention, the system controller 350 is configured to interface with and control the magnification control electronics 315 of the imaging apparatus 310.

In the above description, numerous specific details are given to provide a thorough understanding of embodiments of the invention. However, the above description of illustrated embodiments of the invention is not intended to be exhaustive or to limit the invention to the precise forms disclosed. One skilled in the relevant art will recognize that the invention can be practiced without one or more of the specific details, or with other methods, components, etc.

In other instances, well-known structures or operations are not shown or described in detail to avoid obscuring aspects of the invention. While specific embodiments of, and examples for, the invention are described herein for illustrative purposes, various equivalent modifications are possible within the scope of the invention, as those skilled in the relevant art will recognize.

These modifications can be made to the invention in light of the above detailed description. The terms used in the following claims should not be construed to limit the invention to the specific embodiments disclosed in the specification and the claims. Rather, the scope of the invention is to be determined by the following claims, which are to be construed in accordance with established doctrines of claim interpretation.

What is claimed is:

1. An inspection apparatus for detecting defects in multiple array regions on a manufactured substrate, the apparatus comprising:
   an imaging apparatus arranged to illuminate an area of the substrate and to detect image data from the area, wherein the area includes a set of multiple array regions; and
   a system controller including a processor, memory and computer-readable code in said memory, the computer-readable code being configured to
   determine optimal pixel sizes within an available range of pixel sizes by finding a largest common divider of cell sizes of the multiple array regions when the cell sizes are expressed in integers,
   select an optimal pixel size such that each array region in the multiple array regions has a grouped cell which is an integer number of pixels in size, and
   adjust a pixel size of the imaging apparatus to be the selected optimal pixel size.

2. The inspection apparatus of claim 1, further comprising magnification control electronics for the imaging apparatus, wherein the magnification control electronics is used to adjust the pixel size.

3. The inspection apparatus of claim 1, wherein the imaging apparatus includes a movable substrate holder to move the area of the substrate under the illumination of the imaging apparatus.

4. The inspection apparatus of claim 1, wherein the imaging apparatus comprises an electron beam inspection tool.

5. The imaging apparatus of claim 1, wherein the computer-readable code is further configured to determine a number of cells required to be grouped in each array region based on each optimal pixel size.

6. The imaging apparatus of claim 5, wherein the computer-readable code is further configured to determine which, if any, of the optimal pixel sizes are acceptable based on pre-set criteria.

7. The imaging apparatus of claim 6, wherein the computer-readable code is further configured to choose an acceptable optimal pixel size to be the selected optimal pixel size.

8. The imaging apparatus of claim 6, wherein the computer-readable code is further configured such that, if there is a plurality of acceptable optimal pixel sizes, then one of the acceptable optimal pixel sizes are selected by applying a final criterion.

9. The imaging apparatus of claim 8, wherein applying the final criterion comprises determining which acceptable optimal pixel size provides a least number of total pixels when a number of pixels in the grouped cells from all of the multiple array regions are summed together.

10. The imaging apparatus of claim 6, wherein the computer-readable code is further configured such that, if none of the optimal pixel sizes is determined to be acceptable based on the pre-set criteria, then one of the multiple array regions is marked for digital interpolation.

11. The imaging apparatus of claim 10, wherein the computer-readable code is further configured to modify the set of multiple array regions by removing the marked array region and to select the optimal pixel size based on the modified set of multiple array regions.

12. The imaging apparatus of claim 1, wherein the computer-readable code is configured to select an optimal pixel size in each of two dimensions and to adjust the pixel size of the imaging apparatus in said two dimensions.

13. A method of automatically inspecting multiple array regions simultaneously using an imaging apparatus, the method comprising:
   illuminating an area of the substrate;
   detecting image data from the area, wherein the area includes a set of multiple array regions;
   determining optimal pixel sizes within an available range of pixel sizes by finding a largest common divider of cell sizes of the multiple array regions when the cell sizes are expressed in integers;
   selecting an optimal pixel size such that each array region in the multiple array regions has a grouped cell which is an integer number of pixels in size; and
   adjusting a pixel size of the imaging apparatus to be the selected optimal pixel size.

14. The method of claim 13, further comprising:
   changing a magnification of the imaging apparatus to adjust the pixel size.

15. The method of claim 13, further comprising:
   moving the area of the substrate under the illumination of the imaging apparatus by a movable substrate holder.

16. The method of claim 13, wherein the imaging apparatus comprises:
   an electron beam inspection tool, and the area is illuminated by an electron beam.

17. The method of claim 13, further comprising:
   determining a number of cells required to be grouped in each array region based on each optimal pixel size.

18. The method of claim 17, further comprising:
   determining which, if any, of the optimal pixel sizes are acceptable based on pre-set criteria.

19. The method of claim 18, further comprising:
   choosing an acceptable optimal pixel size to be the selected optimal pixel size.

20. The method of claim 18, further comprising:
   applying a final criterion to select one of the acceptable optimal pixel sizes if there is a plurality of acceptable optimal pixel sizes.

21. The method of claim 20, wherein applying the final criterion comprises determining which acceptable optimal pixel size provides a least number of total pixels when a number of pixels in the grouped cells from all of the multiple array regions are summed together.

22. The method of claim 18, further comprising marking one of the multiple array regions for digital interpolation if none of the optimal pixel sizes is determined to be acceptable based on the pre-set criteria.

23. The method of claim 22, further comprising:
   modifying the set of array regions by removing the marked array region; and
   selecting the optimal pixel size based on the modified set of array regions.

24. The method of claim 13, further comprising:
   selecting an optimal pixel size in each of two dimensions; and
   adjusting the pixel size of the imaging apparatus in said two dimensions.

* * * * *